US009792572B2

(12) United States Patent
Glavina et al.

(10) Patent No.: US 9,792,572 B2
(45) Date of Patent: Oct. 17, 2017

(54) MANAGEMENT SYSTEM FOR POINT OF CARE TESTING

(71) Applicant: Abbott Point of Care Inc., Princeton, NJ (US)

(72) Inventors: Paul Glavina, Ottawa (CA); Jody Ann Tirinato, Plainsboro, NJ (US); Pierre Emeric, Princeton, NJ (US); Dan Molloy, Manchester, NH (US); Maureen Weber, Crete, IL (US); Christopher Fetters, York, PA (US)

(73) Assignee: Abbott Point of Care Inc., Princeton, NJ (US)

( * ) Notice: Subject to any disclaimer, the term of this patent is extended or adjusted under 35 U.S.C. 154(b) by 732 days.

(21) Appl. No.: 14/206,693

(22) Filed: Mar. 12, 2014

(65) Prior Publication Data

US 2014/0278832 A1    Sep. 18, 2014

Related U.S. Application Data

(60) Provisional application No. 61/789,675, filed on Mar. 15, 2013.

(51) Int. Cl.
    G06Q 10/06      (2012.01)
    G06F 19/00      (2011.01)
    G06Q 30/00      (2012.01)

(52) U.S. Cl.
    CPC ....... *G06Q 10/06398* (2013.01); *G06F 19/00* (2013.01); *G06F 19/366* (2013.01); *G06Q 30/018* (2013.01)

(58) Field of Classification Search
    None
    See application file for complete search history.

(56) References Cited

U.S. PATENT DOCUMENTS

| 4,954,087 A | 9/1990 | Lauks et al. |
| 5,096,669 A | 3/1992 | Lauks et al. |
| (Continued) | | |

FOREIGN PATENT DOCUMENTS

| CN | 1755724 | 4/2006 |

OTHER PUBLICATIONS

International Search Report and Written Opinion of the International Searching Authority dated Oct. 31, 2014 for International Patent Application No. PCT/US2014/024433, 11 pages.

*Primary Examiner* — Sujay Koneru
*Assistant Examiner* — Crystol Stewart
(74) *Attorney, Agent, or Firm* — Kilpatrick Townsend & Stockton LLP

(57) ABSTRACT

The present invention relates to a method and system for quality compliance, system and operator verification, and process management for point of care biological sample testing systems used in hospitals and other medical delivery environments. Specifically, the present invention may be directed to a computing device configured to generate a plurality of attributes configured to assess a competency level of an operator to operate at least one sample testing instrument, obtain operator derived data pertaining to the operator's ability to operate the at least one sample testing instrument, and determine a competency level of the operator for the at least one sample testing instrument based the plurality of attributes and the operator derived data.

18 Claims, 6 Drawing Sheets

(56) References Cited

U.S. PATENT DOCUMENTS

| | | | |
|---|---|---|---|
| 6,157,808 A * | 12/2000 | Hollingsworth | G09B 7/02 434/219 |
| 6,953,917 B2 * | 10/2005 | Chenault | B29C 66/9672 219/497 |
| 7,419,821 B2 | 9/2008 | Davis et al. | |
| 8,601,030 B2 * | 12/2013 | Bagchi | G06F 17/30654 706/52 |
| 8,751,408 B2 * | 6/2014 | Linton | G06Q 10/00 705/328 |
| 8,818,837 B2 * | 8/2014 | McCalmont | G06Q 10/0637 705/7.28 |
| 9,390,457 B2 * | 7/2016 | Baym | G06Q 50/22 |
| 9,392,022 B2 * | 7/2016 | Frascadore | H04L 63/20 |
| 2002/0019765 A1 * | 2/2002 | Mann | G06Q 10/06 705/7.14 |
| 2003/0236699 A1 | 12/2003 | Krebs | |
| 2004/0224296 A1 * | 11/2004 | Carraccio | G09B 7/00 434/322 |
| 2005/0033617 A1 * | 2/2005 | Prather | G09B 7/00 434/323 |
| 2007/0105080 A1 * | 5/2007 | Hersh | G09B 7/02 434/236 |
| 2008/0010219 A1 * | 1/2008 | Hargroder | G06Q 10/00 705/76 |
| 2008/0318197 A1 * | 12/2008 | Dion | G09B 7/00 434/322 |
| 2009/0144095 A1 * | 6/2009 | Shahi | G06Q 40/08 705/4 |
| 2009/0299827 A1 * | 12/2009 | Puri | G06Q 10/06398 705/7.42 |
| 2010/0203487 A1 * | 8/2010 | Cyr | G09B 23/286 434/262 |
| 2010/0298956 A1 * | 11/2010 | Van Eeden | G05B 9/03 700/79 |
| 2011/0150705 A1 | 6/2011 | Doyle et al. | |
| 2012/0310700 A1 * | 12/2012 | Kurtz | G06Q 40/08 705/7.28 |
| 2013/0332376 A1 * | 12/2013 | Pilon | G06Q 10/00 705/317 |
| 2013/0343955 A1 | 12/2013 | Doyle et al. | |
| 2014/0101437 A1 * | 4/2014 | Kube | H04L 63/102 713/155 |
| 2014/0272834 A1 * | 9/2014 | Washburn | G09B 23/28 434/219 |
| 2015/0168937 A1 * | 6/2015 | Michalscheck | G05B 19/05 700/83 |

* cited by examiner

MANAGEMENT SYSTEM FOR POINT OF CARE TESTING

CROSS REFERENCE TO RELATED APPLICATIONS

This application claims priority to U.S. Provisional Application No. 61/789,675 filed on Mar. 15, 2013, the entirety of which is incorporated herein by reference.

FIELD OF THE INVENTION

The present invention relates to a method and system for quality compliance, system and operator verification, and process management for point of care biological sample testing systems used in hospitals and other medical delivery environments. Specifically, the present invention relates to portable blood testing instrumentation that works in conjunction with consumable cartridges and how this is efficiently achieved in a modern regulatory environment.

BACKGROUND OF THE INVENTION

For hospitals, the introduction of point-of-care testing capabilities has created unique requirements and issues for quality compliance, system and operator verification, and process management. These issues arise from the use of a plurality of instruments running multiple types of disposable sample testing devices at various locations within a hospital. Consequently, a hospital must provide an adequate supply of each type of device at each site of use, while ensuring the devices are within their usable shelf-life, along with also ensuring that the instruments are performing to specification. A further consideration is ensuring that each user of the technology, or operator, is properly qualified to do so and maintains a valid training record.

Point-of-care sample analysis systems are generally based on a re-usable reading apparatus that performs sample tests using a single-use disposable device, e.g., a cartridge or strip that contains analytical elements, e.g., electrodes or optics for sensing analytes such as pH, oxygen and glucose. The disposable device can include fluidic elements (e.g., conduits for receiving and delivering the sample to sensing electrodes or optics), calibrant elements (e.g., aqueous fluids for standardizing the electrodes with a known concentration of analyte), and dyes with known extinction coefficients for standardizing optics. The reading apparatus or instrument contains electrical circuitry and other components for operating the electrodes or optics, making measurements, and doing computations. The reading apparatus also has the ability to display results and communicate those results to laboratory and hospital information systems (LIS and HIS, respectively), for example, via a computer workstation or other data management system. Communication between the reading apparatus and a workstation, and between the workstation and a LIS, can be via, for example, an infrared link, a wired connection, wireless communication, or any other form of data communication that is capable of transmitting and receiving electrical information, or any combination thereof. A notable point-of-care system (The i-STAT® System, Abbott Point of Care Inc., Princeton, N.J.) is disclosed in U.S. Pat. No. 5,096,669, which comprises a disposable device, operating in conjunction with a hand-held analyzer, for performing a variety of measurements on blood or other fluids.

One benefit of point-of-care sample testing systems is the elimination of the time-consuming need to send a sample to a central laboratory for testing. Point-of-care sample testing systems allow a nurse or doctor (user or operator), at the bedside of a patient, to obtain a reliable quantitative analytical result, comparable in quality to that which would be obtained in a laboratory. In operation, the nurse selects a device with the required panel of tests, draws a biological sample from the patient, dispenses it into the device, optionally seals the device, and inserts the device into the reading apparatus. While the particular order in which the steps occur may vary between different point-of-care systems and providers, the intent of providing rapid sample test results close to the location of the patient remains. The reading apparatus then performs a test cycle, i.e., all the other analytical steps required to perform the tests. Such simplicity gives the doctor quicker insight into a patient's physiological status and, by reducing the time for diagnosis or monitoring, enables a quicker decision by the doctor on the appropriate treatment, thus enhancing the likelihood of a successful patient outcome.

In the emergency room and other acute-care locations within a hospital, the types of sample tests required for individual patients tend to vary. Thus, point-of-care systems generally offer a range of disposable devices with different sample tests, or combinations of tests. For example, for blood analysis devices, in addition to traditional blood tests, including oxygen, carbon dioxide, pH, potassium, sodium, chloride, hematocrit, glucose, urea, creatinine and calcium, other tests can include, for example, prothrombin time (PT), activated clotting time (ACT), activated partial thromboplastin time (APTT), cardiac troponin I (cTnI), brain natriuretic peptide (BNP), creatine kinase MB (CKMB) and lactate. While devices typically contain between one and ten tests, it should be appreciated by persons of ordinary skill in the art that any number of tests may be contained on a device. For example, a device for genetic screening may include numerous tests. To illustrate the need for different devices, a patient suspected of arrhythmia may require a device with a test combination that includes a potassium test, whereas a patient suspected of a diabetic hypoglycemia may require a device with a test combination that includes a glucose test. An emergency room will need to have sufficient inventory of both types of device to meet the anticipated workload.

Quality compliance, system verification and process management at the point-of-care has traditionally relied on direct human intervention. Typically, a person from the hospital central laboratory, e.g., a designated point-of-care testing coordinator, would be responsible for regularly visiting point-of-care testing locations to track performance. Because of the substantially manual nature of this approach, there are several opportunities for delay and possible human error. The present invention seeks to ameliorate these problems and provide a substantially automated system for quality compliance, operator and system verification, and process management.

SUMMARY OF THE INVENTION

In one embodiment, the present invention may be directed to a method implemented in a computer infrastructure having computer executable code tangibly embodied on a computer readable storage medium having programming instructions operable to generate a plurality of attributes configured to assess a competency level of an operator to operate at least one sample testing instrument and set a compliance threshold for the at least one sample testing instrument. The programming instructions may be further operable to obtain operator derived data pertaining to the operator's ability to operate the at least one sample testing instrument. The operator derived data may comprise at least two attribute test results obtained by the operator. The programming instructions may be further operable to determine a compliance status of the operator for the plurality of attributes based on the obtained operator derived data, and determine the competency level of the operator for the at least one sample testing instrument based on a comparison of the compliance status of the operator to the set compliance threshold. The programming instructions may be further operable to communicate the competency level of the operator to the at least one sample testing instrument.

In some aspects, the generating the plurality of attributes may comprise selecting at least two attributes from the group consisting of: a knowledge test for operation of the at least one instrument, a knowledge test for biological sample acquisition and disposition with the at least one instrument, a knowledge test on biological sample testing regulations, a practical test on obtaining biological sample test results with the at least one instrument, a practical test on quality control testing with the at least one instrument, a practical test on data entry, and data handling with the at least one instrument.

In some embodiments, each attribute of the plurality of attributes may comprise an electronic signature element, and the determining the compliance status of the operator may further comprises determining whether the electronic signature element for each attribute is completed by an authorized user.

In addition, optionally the set compliance threshold may comprise any combination of at least two attributes having an approved compliance status, and the determining the competency level may comprise that when the compliance status includes at least two attributes having an approved compliance status, determining the competency level to be compliant, and when the compliance status includes less than two attributes having an approved compliance status, determining the competency level to be non-compliant.

In another embodiment, a method of deploying a system for assessing competency of an operator to operate at least one sample testing instrument may be provided. The method may comprise providing a computer infrastructure, being operable to generate a plurality of attributes configured to assess the competency of the operator to operate the at least one sample testing instrument, set a compliance threshold for each attribute of the plurality of attributes, set an overall compliance threshold for the at least one sample testing instrument, and obtain operator derived data pertaining to the operator's ability to operate the at least one sample testing instrument. The computer infrastructure may be further operable to compare the operator derived data to the set compliance threshold for each attribute of the plurality of attributes, determine a compliance status of the operator for each attribute based on the comparison of the operator derived data to the set compliance thresholds, generate an overall compliance status of the operator based on the determined compliance status of the operator for each attribute, and compare the overall compliance status of the operator to the set overall compliance threshold for the at least one sample testing instrument. The computer infrastructure may be further operable to determine a competency level of the operator for the at least one sample testing instrument based on the comparison of the overall compliance status of the operator to the set overall compliance threshold, and communicate the competency level of the operator to the at least one sample testing instrument.

In another embodiment, a method of deploying a system for compliance monitoring may be provided. The method may comprise providing a computer infrastructure being operable to generate a plurality of attributes configured to assess a competency of an operator to operate at least one sample testing instrument, set an overall compliance threshold for the at least one sample testing instrument, and obtain operator derived data pertaining to the operator's ability to operate the at least one sample testing instrument. The operator derived data may comprise at least two attribute test results obtained by the operator, and a corresponding operator identifier configured to identify the operator. The computer infrastructure may be further operable to determine a compliance status of the operator for the plurality of attributes based on the obtained operator derived data, determine a competency level of the operator for the at least one sample testing instrument based on a comparison of the compliance status of the operator to the set overall compliance threshold, and communicate the competency level of the operator to the at least one sample testing instrument. The method may further comprise providing the at least one sample testing instrument being operable to receive input including the operator identifier configured to identify the operator, analyze the biological sample, determine at least one test result, communicate the at least one test result to the computer infrastructure, receive the competency level of the operator, and lock the user from operating the at least one sample testing instrument when the competency level is non-compliant.

In another embodiment, a system may be provided implemented in hardware and comprising a tracking module configured to generate a plurality of attributes configured to assess a competency level of an operator to operate at least one sample testing instrument and set a compliance threshold for the at least one sample testing instrument. The tracking module may be further configured to obtain operator derived data pertaining to the operator's ability to operate the at least one sample testing instrument. The operator derived data may comprise at least two attribute test results obtained by the operator. The tracking module may be further configured to determine a compliance status of the operator for the plurality of attributes based on the obtained operator derived data, determine the competency level of the operator for the at least one sample testing instrument based on a comparison of the compliance status of the operator to the set compliance threshold, and communicate the competency level of the operator to the at least one sample testing instrument.

In addition, optionally the at least two attribute test results may be linked to a corresponding operator identifier configured to identify the operator, and the step of obtaining the operator derived data may comprise receiving the at least two test attribute results and the operator identifier.

In some embodiments, the set compliance threshold may comprise any combination of at least two attributes having an approved compliance status, and the step of determining the competency level may comprise determining the competency level to be compliant when the compliance status includes at least two attributes having an approved compliance status, and determining the competency level to be non-compliant when the compliance status includes less than two attributes having an approved compliance status.

In another embodiment, a system may be provided implemented in hardware comprising at least one sample testing instrument configured to receive input including an operator identifier configured to identify an operator of the at least one sample testing instrument, analyze a biological sample, determine at least one test result for the biological sample, and communicate the at least one test result. The system may also comprise a tracking module configured to generate a plurality of attributes configured to assess a competency level of the operator to operate the at least one sample testing instrument, set a compliance threshold for the at least one sample testing instrument, and obtain operator derived data pertaining to the operator's ability to operate the at least one sample testing instrument. The operator derived data may comprise the at least one test result communicated by the at least one sample testing instrument. The tracking module may also be configured to determine a compliance status of the operator for the plurality of attributes based on the obtained operator derived data, determine the competency level of the operator for the at least one sample testing instrument based on a comparison of the compliance status of the operator to the set compliance threshold, and communicate the competency level of the operator to the at least one sample testing instrument may be further configured to receive the competency level of the operator, and lock the operator from further operating the at least one instrument when the competency level is non-compliant.

In another embodiment, the present invention may be directed to computer system for assessing competency of an operator to operate at least one sample testing instrument. The system may comprise a CPU, a computer readable memory and a computer readable storage media. The system may further comprise first program instructions to generate a plurality of attributes configured to assess the competency of the operator to operate the at least one sample testing instrument, second program instructions to set a compliance threshold for each attribute of the plurality of attributes, third program instructions to set an overall compliance threshold for the at least one sample testing instrument, fourth program instructions to obtain operator derived data pertaining to the operator's ability to operate the at least one sample testing instrument, fifth program instructions to compare the operator derived data to the set compliance threshold for each attribute of the plurality of attributes, sixth program instructions to determine a compliance status of the operator for each attribute based on the comparison of the operator derived data to the set compliance thresholds, seventh program instructions to generate an overall compliance status of the operator based on the determined compliance status of the operator for each attribute, eighth program instructions to compare the overall compliance status of the operator to the set overall compliance threshold for the at least one sample testing instrument, ninth program instructions to determine a competency level of the operator for the at least one sample testing instrument based on the comparison of the overall compliance status of the operator to the set overall compliance threshold, and tenth program instructions to communicate the competency level of the operator to the at least one sample testing instrument. The first through tenth program instructions may be stored on the computer readable storage media for execution by the CPU via the computer readable memory.

In yet another embodiment, the present invention may be directed to computer program product comprising a computer readable storage medium having readable program code embodied in the storage medium. The computer program product may include at least one component operable to generate a plurality of attributes configured to assess a competency level of an operator to operate at least one sample testing instrument, set a compliance threshold for the at least one sample testing instrument, and obtain operator derived data pertaining to the operator's ability to operate the at least one sample testing instrument. The operator derived data comprises at least two attribute test results obtained by the operator. The at least one component may be further operable to determine a compliance status of the operator for the plurality of attributes based on the obtained operator derived data, determine the competency level of the operator for the at least one sample testing instrument based on a comparison of the compliance status of the operator to the set compliance threshold, and communicate the competency level of the operator to the at least one sample testing instrument.

BRIEF DESCRIPTION OF THE DRAWINGS

The present invention will be better understood in view of the following non-limiting figures, in which.

DETAILED DESCRIPTION OF THE INVENTION

Introduction

Figure 1:
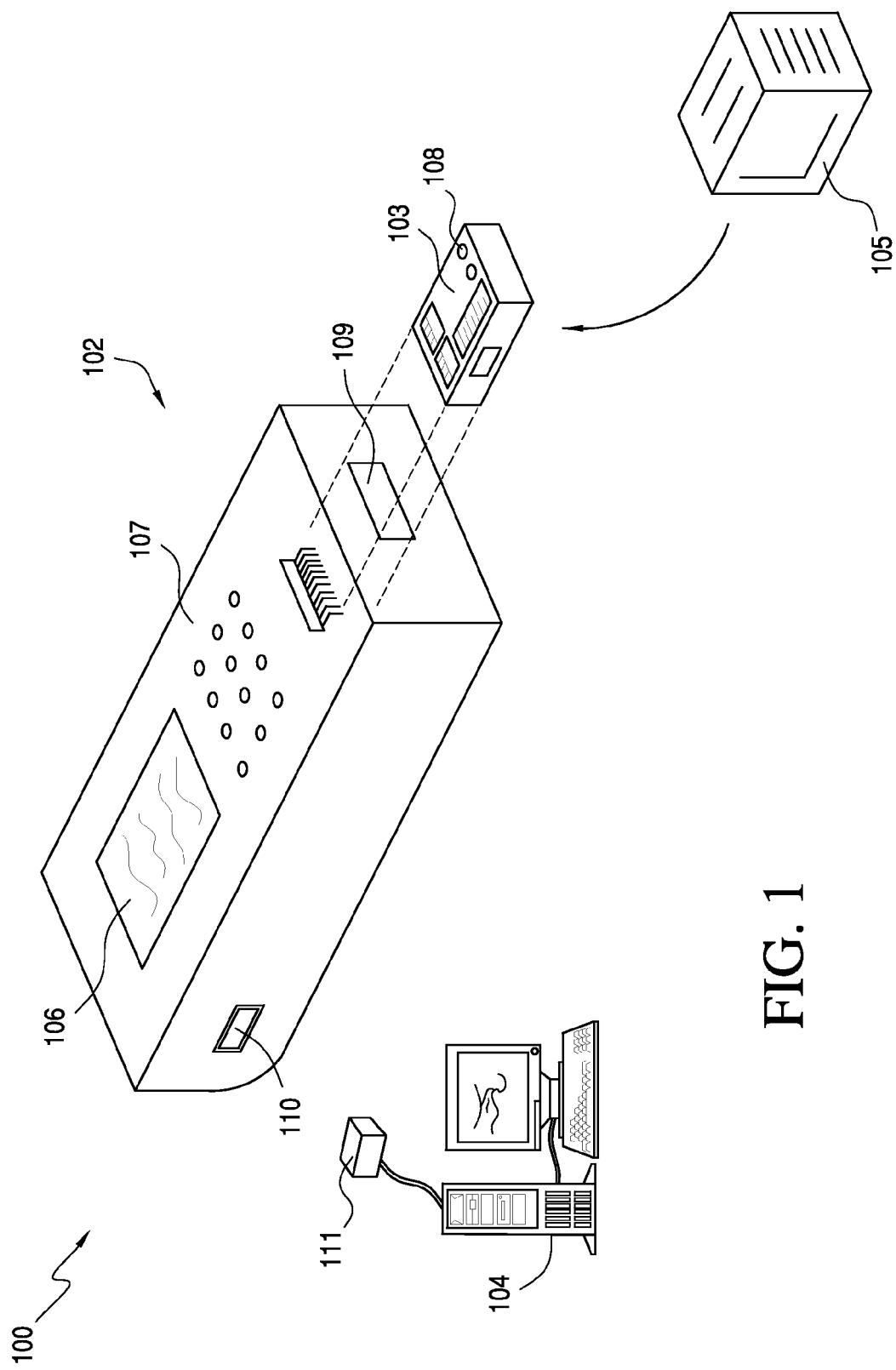
FIG. 1 shows an isometric view of a disposable sensing device and reader device in accordance with some aspects of the invention.

A typical point of care testing program in an institution may have tens or hundreds of non-laboratory operators with wide ranges of education, training, responsibilities, and understanding of medical conditions and the indications and implications of medical testing. A challenge of any program for quality compliance is the initial training of the operators and the ongoing assessment of their testing competency. Typically, this is a responsibility of a quality compliance manager in partnership with nursing and other clinical personnel, who manually construct and implement a meaningful competency assessment process.

The present invention is directed to providing a computing tool configured to help quality compliance managers to efficiently and effectively construct, implement, and maintain a meaningful competency assessment process. Competency assessment may include the evaluation of an individual's knowledge, skills, and correct practice of required processes and procedures. Typically, competency assessment programs include evaluating the competency of all testing personnel and assuring that the staff maintains their competency to perform test procedures and report result promptly, accurately, and proficiently.

Some embodiments of the present invention are directed to utilizing the computing tool to develop a competency assessment program that includes a plurality of attributes configured to assess a competency level of at least one operator to operate at least one sample testing instrument. In accordance with these aspects of the present invention, the plurality of attributes may be constructed to provide an evaluation of an operator's knowledge, skills, and correct practice of required processes and procedures with respect to the at least one sample testing instrument. For example, the plurality of attributes may include procedures for assessing competency as mandated by the Clinical Laboratory Improvement Act. More specifically, in some embodiments, the plurality of attributes may include methods for assessing competency including direct observation of routine patient test performance, including testing performance and monitoring the recording of the results (e.g., this may include recording all test results performed by the operator on a sample testing instrument and monitoring the results for any instrument reported errors). The plurality of attributes may also include the review of intermediate test results, quality control results, proficiency testing results, and preventive maintenance records (e.g., this may include recording all of these results performed by the operator and monitoring the results for inaccuracies). The plurality of attributes may also include observation of performance of instrument maintenance and function checks (e.g., this may include recording the results of knowledge tests for operation of the at least one instrument). The plurality of attributes may also include the assessment of problem solving skills (e.g., this may include recording the results of knowledge tests for biological sample acquisition and disposition with the at least one instrument and knowledge tests on biological sample testing regulations). Although the plurality of attributes are described herein with respect to the above-mentioned examples, it should be understood by those of ordinary skill in the art that such examples are non-limiting, and the attributes may be designed in any manner so long as they are configured to provide procedures for assessing competency of an operator operating a sample testing instrument in accordance with the various aspects of the present invention.

A central data management system that comprises the computing tool may be configured to automatically keep track of the plurality of attributes and compliance thresholds (e.g., a means for evaluating compliance or non-compliance with operation of the sample testing instruments) associated with each sample testing instrument within the testing program. In some embodiments, the central data management system may also keep track of records for each operator within the testing program using an operator tracking record and/or profile system.

The records may include each operator's competency level for sample testing instruments, results of knowledge tests, analytical test results, clinical control results, proficiency test results, etc. It should be understood by those of ordinary skill in the art that the knowledge test or knowledge test results may pertain to written or training proficiency tests that provide an evaluation of an operator's knowledge of a certain aspect of diagnostic testing involving the sample testing instrument (e.g., a knowledge test for biological sample acquisition and disposition with the instrument); the analytical test or analytical test results may pertain to clinical diagnostic tests run on a sample (e.g., a blood sample from a patient) using the sample testing instrument; the control tests or control test results may pertain to quality control measures designed to minimize the effects of variables during the clinical diagnostic tests (e.g., running a control sample having a known analyte concentration using the sample testing instrument); and the proficiency tests or proficiency test results may pertain to testing previously analyzed specimens with known concentrations of analyte, internal blind testing samples, or external proficiency testing samples configured for statistical quality assurance programs that enable laboratories to assess their performance in conducting test methods.

In various embodiments, the central data management system may be further configured to determine the competency level of the operator for sample testing instruments using the plurality of attributes and compliance thresholds, and automatically convey the competency level of the operator to the sample testing instruments. In additional embodiments, the sample testing instruments may be configured to lock the user from operating the sample testing instruments in the instance that the operator has been determine to be non-compliant with the plurality of attributes developed by the quality compliance manager.

Advantageously, the present invention is able to provide a point of care quality system that consistently implements the competency assessment plan, and provides an electronic means for tracking and documenting competency assessment records to assist in implementing the plan. Even more advantageously, the present invention is able to provide a point of care quality system that ensures employees perform critical tasks accurately by locking non-compliant employees out from performing such critical tasks (e.g., operating sample testing instruments).

Biological Sample Test System

The present invention relates to a handheld In-Vitro Diagnostic (IVD) instrument system including a self-contained disposable sensing device or cartridge and a reader or analyzer configured for use at a patient bedside. A fluid sample to be measured is drawn into a sample entry orifice or port in the cartridge and the cartridge is inserted into the analyzer through a slotted opening or port. Measurements performed by the analyzer are output to a display or other output device, such as a printer or data management system via a port on the analyzer to a computer port. Transmission can be via Wifi, Bluetooth link, infrared and the like. For example, the handheld IVD instrument system may be of similar design to the systems disclosed in U.S. Pat. No. 5,096,669 and U.S. Pat. No. 7,419,821, both of which are incorporated herein by reference in their entireties.

More specifically, a system and method are disclosed for operating a plurality of point-of-care diagnostic devices (e.g., cartridges). Each device may be configured to perform at least one biological sample analysis, e.g., blood, plasma, urine tests and the like, and each device may have a usable lifetime. FIG. 1 shows the component parts and interactions of a typical point-of-care system. The system 100 may include a reading apparatus 102, a disposable device 103, a central data station or data manager 104 and a box of devices 105. The reading apparatus 102 may include, for example, a display 106, electronic memory and a keypad 107 for manual data entry. The disposable device 103 may include, for example, a port 108 for receiving a patient sample, and the device 103 may be inserted into the reading apparatus 102 through a slotted opening 109. The reading apparatus 102 may communicate with the central data manager 104 using, for example, a wireless connection, an infrared link, an optical link, a network connection 110, 111, or any other form of communication link that uses any form of communication protocol to transfer information.

The reading apparatus 102 may include a barcode reader for reading information from a patient's bar-coded wristband, from a barcode on a device 103 or from any other item (e.g., the box of devices 105, box of control fluids, etc.) used in conjunction with the reading apparatus 102. Other such encoding arrangements can be used. For example, the reading apparatus 102 may also include (either alternatively or in addition to the barcode reader) a radio-frequency (RF) identification device that is capable of identifying a RF tag that is contained on or in each individual device or each box of devices 108. According to another exemplary embodiment of the present invention, one or more of the encoding arrangements may be based upon a binary coding pin array of the type disclosed in, for example, U.S. Pat. No. 4,954,087, which is incorporated herein by reference in its entirety.

The various encoding arrangements may convey relevant information such as, for example, the identity of a specific device type, date and location of manufacture, manufacturing lot number, expiration date, a unique number associated with a device, coefficients for use by the reading apparatus 102 associated with the calculation of blood or other sample parameters and the like. The devices may be used for measurements selected from groups such as, for example, amperometric, potentiometric, conductimetric, optical and the like. Other relevant information of this general type is well known in the medical manufacturing art, as is the technology for bar coding and barcode recognition.

Other information encoded with the device may include the refrigerator shelf life, the ambient temperature shelf life, the age of the device and the like. Alternatively, rather than including numerous elements of relevant information, a single piece of information, e.g., a lot number, may be included. The lot number may be any alphanumeric sequence or unique identifier that can be used to identify the device 104 and associate relevant information with that device. For example, the lot number can be applied to a lookup table or any other type of computer database located within or connected to the reading apparatus 102 or any other computing system, e.g., the data manager 104. Using the lookup table or computer database, relevant shelf life or other such information can be associated with the lot number such that, based on the lot number, the refrigerator shelf life, the ambient temperature shelf life, the age of the device 103 and the like can be determined.

The devices 103 may have a finite refrigerator and ambient temperature shelf life. For example, the devices 103 may have a refrigerated usable lifetime in the range of, for example, about three months to three years, although the devices 103 could have any range of refrigerated usable lifetime. The devices 103 may have an ambient temperature usable lifetime in the range of, for example, about three days to three months, although the devices 103 can have any range of ambient temperature usable lifetime. Given that the devices 103 may have a finite refrigerator and ambient temperature shelf life, there may be a need to ensure that expired devices 103 (e.g., the devices 103 that have exceeded the refrigerated or ambient temperature shelf life) are not used.

Referring to the disposable device 103 and the patient sample entry port 108, the device 103 may perform analyses on a range of biological sample types. These sample types may include, for example, blood, plasma, serum, sputum, cerebrospinal fluid, tears, urine, body tissue, and fecal matter and the like. Appropriate consumable items for use in conjunction with the device 103 are well known in the art. These include, for example, vacutainers, needles, capillary tubes and collection devices, control fluids of different types, syringes, swabs, printer paper, batteries and any other consumable item that can be used in conjunction with the device 103. The consumable items can also be used to facilitate introduction of the sample into the sample entry port 108.

The reading apparatus 102 may include a microprocessor (e.g., any type of processor). The reading apparatus may also include any type of computer memory or any other type of electronic storage medium that is located either internally or externally to the reading apparatus 102, such as, for example, a random access memory (RAM). According to exemplary embodiments, the RAM may contain, for example, the operating program for the reading apparatus 102. As will be appreciated based on the following description, the RAM can, for example, be programmed using conventional techniques known to those having ordinary skill in the art of computer programming. The actual source code or object code for carrying out the steps of, for example, a computer program can be stored in the RAM.

The reading apparatus 102 may include a communications port (e.g., any type of communications port through which electronic information can be communicated over a communications connection, whether locally or remotely) with which the reading apparatus 102 can communicate with, for example, the data manager 104. The reading apparatus 102 may also include the input port 109 that, for example, allows insertion of the device 103 and is appropriately configured to receive the device 103. The reading apparatus 102 may also include a user interface. The user interface may be any type of computer monitor or display device on which graphical and/or textual information can be displayed to a user (e.g., through a graphical user interface) and which allows a user to enter information (e.g., commands and the like) through, for example, a keyboard, a touch-screen, any type of pointing device, electronic pen, and the like. For example, the user interface can be configured to receive instructions from the operator of the reading apparatus 102. It should also be appreciated that, while a single reading apparatus 102 is described above, multiple reading apparatus 102 can be included within a system where each is connected to the data manager 104. Typically, each department within a hospital may have one or more readers.

It should further be appreciated by persons of ordinary skill in the art that the devices 103, may in fact be a plurality with each type capable of being used for a different test. The devices 103 can include, for example, blood analysis devices, urine analysis devices, serum analysis devices, plasma analysis devices, saliva analysis devices, cheek swab analysis devices, or any other type of disposable diagnostic device that can be used for point-of-care sample testing.

The data manager 104 may be configured to provide connectivity between individual reading apparatus 102 and central locations, such as, for example, a LIS or HIS, and device 103. The data manager 104 may be connected with the various system constituents using any type of communications connection that is capable of transmitting and receiving electronic information, such as, for example, an Ethernet connection or other computer network connection. The data manager 104 can also optionally provide a direct link back to a vendor's information system, for example via the Internet, a dial-up connection or other direct or indirect communication link, or through the LIS or HIS. Such an exemplary embodiment can provide for automated re-ordering of devices 103 to maintain the predetermined levels of inventory at a hospital and allow the vendor to forecast demand and adequately plan the manufacture of the devices 103.

Exemplary Device or Cartridge

Figure 2:
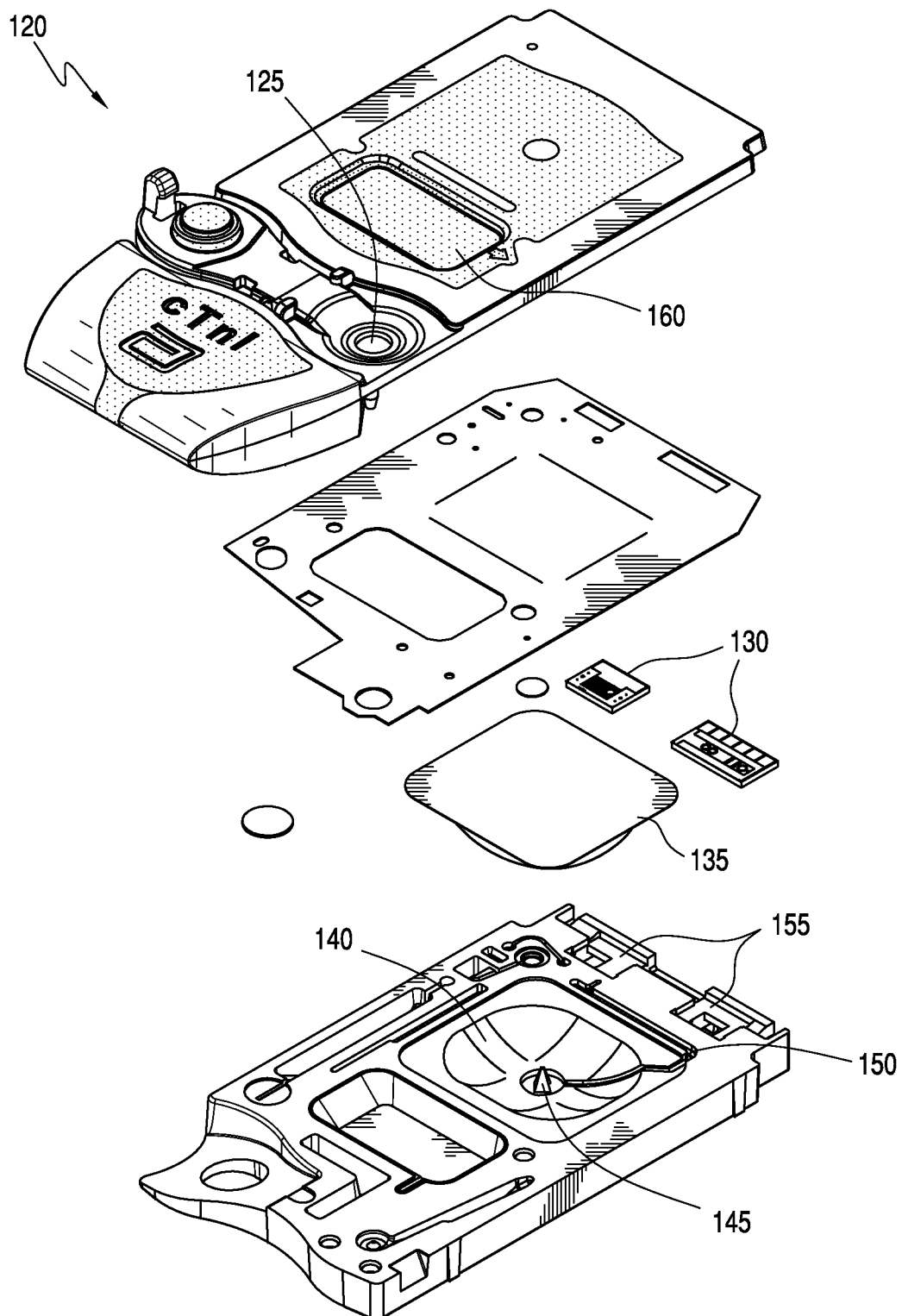
FIG. 2 shows an exploded view of a cartridge in accordance with some aspects of the invention.

FIG. 2 shows an exploded view of cartridge 120 as described U.S. Patent Application Publication No. 2011/0150705 and U.S. patent application Ser. No. 13/530,501. The cartridge 120 comprises a sample entry port 125, at least one sensor 130 (e.g., an electrochemical sensor, an immunosensor, a hematocrit sensor, a conductivity sensor, etc.), and a pouch 135 containing a fluid, e.g., a sensor-standardization, calibration fluid, and/or wash fluid. The at least one sensor 130 may be substantially aligned to a plane parallel to a horizontal plane of the base of the analyzer. A recessed region 140 of the cartridge 120 preferably includes a spike 145 configured to rupture the pouch 135, upon application of a force upon the pouch 135, for example, by the analyzer 102 (shown in FIG. 1). Once the pouch 135 is ruptured, the system is configured to deliver the fluid contents from the pouch 135 into a conduit 150. Movement of the fluid into and through the conduit 150 and to a sensor region 155 (e.g., a conduit comprising the at least one sensor 130 and a sensing reagent for the sensor) may be effected by a pump, e.g., a pneumatic pump connected to the conduit 150. Preferably, the pneumatic pump comprises a displaceable membrane 160. In the embodiment shown in FIG. 2, the cartridge 120 or test device may be configured to pump fluid via the displaceable membrane 160 from the ruptured pouch 135 and the sample entry port 125 through the conduit 150 and over the sensor region 155. The at least one sensor 130 generates electric signals based on a concentration of specific chemical species in the sample, e.g., performs an immunoassay on a blood sample from a patient.

The analytes/properties to which the at least one sensor responds generally may be selected from among hematocrit, troponin, CKMB, BNP, beta human chorionic gonadotropin (bHCG), carbon dioxide partial pressure ($pCO_2$), partial pressure oxygen ($pO_2$), pH, PT, ACT, activated partial thromboplastin time (APTT), sodium, potassium, chloride, calcium, urea, glucose, creatinine, lactate, oxygen, and carbon dioxide, thyroid stimulating hormone, parathyroid hormone, D-dimer, prostate specific antibody and the like, and combinations thereof. Preferably, the analyte is tested in a liquid sample that is whole blood, however other samples can be used including blood, plasma, serum, sputum, cerebrospinal fluid, tears, urine, body tissue, and fecal matter and amended forms thereof. Amendments can include diluents and reagents such as anticoagulants and the like.

System Environment

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, RAM, a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 3:
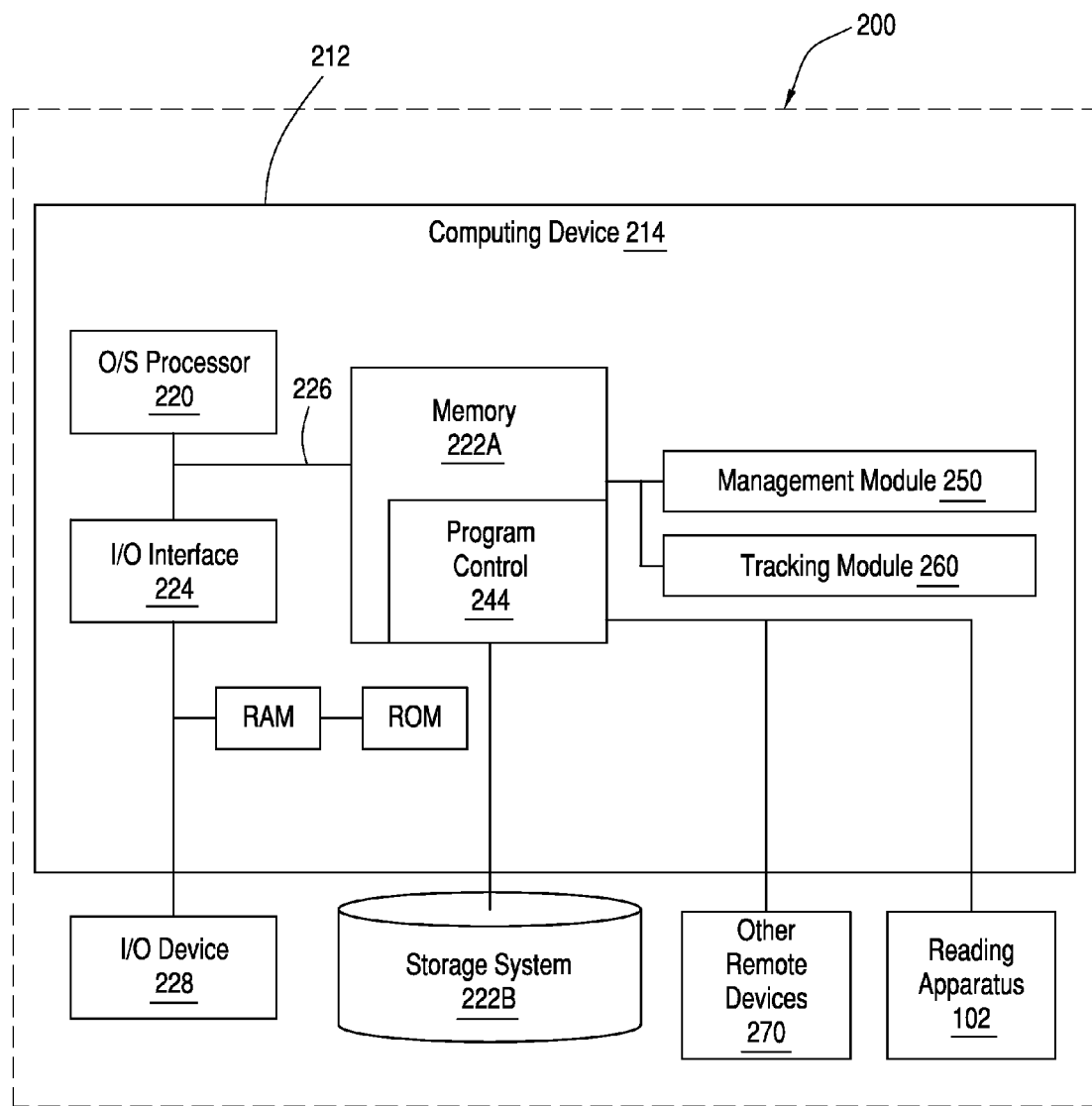
FIG. 3 is an illustrative external environment for implementing the invention in accordance with some aspects of the invention.

FIG. 3 shows an illustrative environment 200 for managing the processes in accordance with the invention. To this extent, the environment 200 includes a server or other computing system 212 that can perform the processes described herein. In particular, the server 212 includes a computing device 214 (e.g., the data manager 104). The computing device 214 can be resident on a network infrastructure or computing device of a third party service provider (any of which is generally represented in FIG. 3).

The computing device 214 also includes a processor 220, memory 222A, an I/O interface 224, and a bus 226. The memory 222A can include local memory employed during actual execution of program code, bulk storage, and cache memories which provide temporary storage of at least some program code in order to reduce the number of times code must be retrieved from bulk storage during execution. In addition, the computing device 214 includes RAM, ROM, and an operating system (O/S).

The computing device 214 may be in communication with an external I/O device/resource 228 and the storage system 222B. For example, the I/O device 228 can comprise any device that enables an individual to interact with the computing device 214 or any device that enables the computing device 214 to communicate with one or more other computing devices using any type of communications link. The external I/O device/resource 228 may be for example, a handheld device, PDA, handset, mechanical keyboard, etc.

In general, the processor 220 executes computer program code (e.g., program control 244), which can be stored in the memory 222A and/or storage system 222B. Moreover, in accordance with aspects of the invention, the program control 244 may communicate with a management module 250, tracking module 260, the reading apparatus 102, and or other remote devices 270 such as operator's personal computer or mobile device. The management module 250 and tracking module 260 can be implemented as one or more program code in the program control 244 stored in memory 222A as separate or combined modules. Additionally, the management module 250 and tracking module 260 may be implemented as separate dedicated processors or a single or several processors to provide the function of these modules. In embodiments, the management module 250 and tracking module 260 may be configured to carry out the processes of the present invention discussed in further detail herein. While executing the computer program code, the processor 220 can read and/or write data to/from memory 222A, storage system 222B, and/or I/O interface 224. The program code executes the processes of the invention. The bus 226 provides a communications link between each of the components in the computing device 214.

The computing device 214 can comprise any general purpose computing article of manufacture capable of executing computer program code installed thereon (e.g., a personal computer, a smartphone, a laptop, a tablet, etc.). However, it is understood that computing device 214 is only representative of various possible equivalent-computing devices that may perform the processes described herein. To this extent, in some embodiments, the functionality provided by computing device 214 can be implemented by a computing article of manufacture that includes any combination of general and/or specific purpose hardware and/or computer program code. In each embodiment, the program code and hardware can be created using standard programming and engineering techniques, respectively.

Similarly, computing infrastructure 212 is only illustrative of various types of computer infrastructures for implementing the invention. For example, in embodiments, server 212 comprises two or more computing devices (e.g., a server cluster) that communicate over any type of communications link, such as a network, a shared memory, or the like, to perform the process described herein. Further, while performing the processes described herein, one or more computing devices on server 212 can communicate with one or more other computing devices external to server 212 using any type of communications link. The communications link can comprise any combination of wired and/or wireless links; any combination of one or more types of networks (e.g., the Internet, a wide area network, a local area network, a virtual private network, etc.); and/or utilize any combination of transmission techniques and protocols.

Instrument and Cartridge Operator Competency and Compliance Monitoring System

Figure 4:
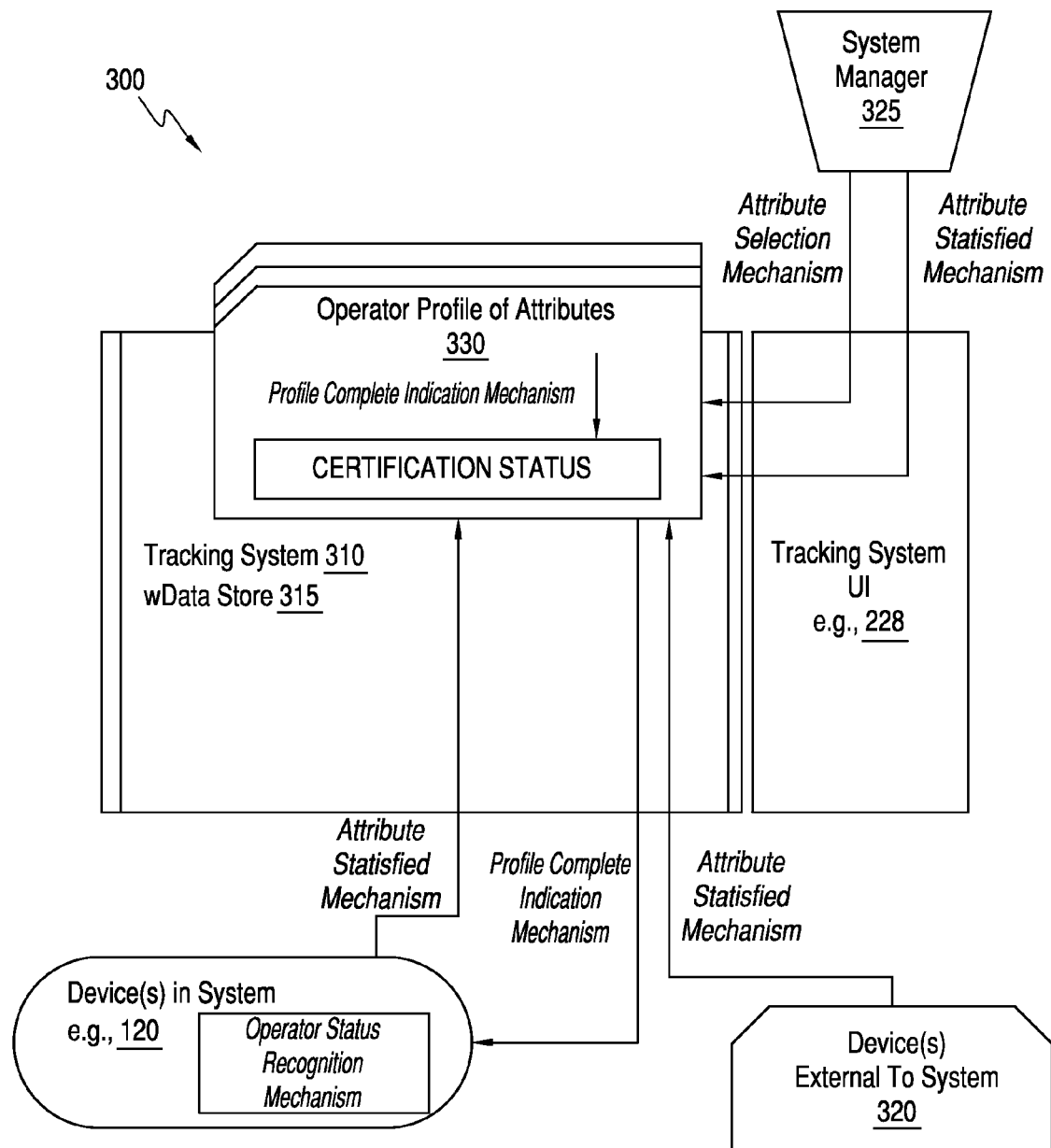
FIG. 4 is a block diagram illustrating an operator compliance monitoring system for a point-of-care diagnostic technology, in accordance with some aspects of the invention.

FIG. 4 shows an exemplary compliance monitoring system 300 in accordance with some aspects of the present invention. The compliance monitoring system 300 is configured to ensure that an operator is properly qualified to operate a biological sample testing system (e.g., system 100 as discussed with respect to FIG. 1). The operator compliance monitoring system 300 may be conceived for distributed or point of care analytical testing with a plurality of portable test instruments (e.g., sample testing instrument or reading apparatus 102), typically located in a medical facility. The compliance monitoring system 300 may comprise a data tracking system 310 with an operator tracking record (e.g., management module 250 and/or tracking module 260 as discussed with respect to FIG. 3) and may have a plurality of attributes required for compliance by the operator when using one or more of the portable test instruments 102. Specifically, the tracking system 310 may comprise a testing results store 315, which can communicate in a monodirectional or bi-directional manner with devices internal to the system 300 including the portable test instruments 102 and other devices 320 external to the system 300 (e.g., external computing devices that could send data to the data tracking system 310, such as Knowledge Management systems having on-line quiz results, in-service training event completion, etc.). The plurality of attributes for each operator (e.g., user, nurse, doctor, etc.) in the data tracking system 310 may be selected by a data tracking system manager or quality compliance manager 325 (e.g., a supervisor or trainer) and communicated from the compliance monitoring system 310 to the portable test instruments 102. In circumstances of compliance by the operator, the compliance monitoring system 300 may permit use of at least one of the portable test instruments 102, whereas non-compliance may automatically lock out the operator from use of at least one of the instruments 102.

Several other features of the compliance monitoring system may include that each required attribute have an electronic signature element operable by designated super-users, trainers, nurse managers, or system managers, each required attribute may have an electronic logging element, and each required attribute may be selected from, for example, a set of competency requirements from the College of American Pathologists, such as: Direct observations of routine patient test performance, including patient preparation, if applicable, specimen handling, processing and testing; Monitoring the recording and reporting of test results; Review of intermediate test results or worksheets, quality control records, proficiency testing results and preventive maintenance records; Direct observation of performance of instrument maintenance and function checks; Assessment of test performance through testing previously analyzed specimens, internal blind testing samples or external proficiency testing samples; and Evaluation of problem-solving skills.

In addition, the required attributes may be updatable by the system manager 325, communicated to the instruments 102, and displayed for the operator. Advantageously, the compliance monitoring system 300 allows for automatic tracking of operator compliance for a plurality of operators, e.g., as many as a hundred nurses in a single hospital. Furthermore, each portable test instrument 102 may be configured to communicate each blood test result and operator identity to the results store 315 in the data tracking system 310 such that an operator tracking record or events profile 330 may be generated for each operator, monitoring both compliant events and non-compliant events.

With regard to system updates, each use of the portable test instrument 102 by the operator can optionally cause the instrument to communicate with the data tracking system 310 to update the operator tracking record 330. This can include a sample test result being sent and stored in the tracking system 310. With regard to the attributes in the data tracking system 310, these may generally initially be set to a standard default setting or template and the system manager may generally retain the default settings. However, the system manager may create new attributes and/or customize the settings of the attributes for a given medical facility. When a required attribute is updatable by the system manager 325, the updated required attribute may be communicated to the instrument 102 and displayed for the operator. In some embodiments, each of the attributes may have a non-compliance or compliance threshold, and a combination of at least a certain number of (e.g., two) exceeded or non-exceeded thresholds may be determinative of a lock out of the operator from the instrument. In alternative embodiments, each of the attributes may have a non-compliance or compliance threshold, and a statistical combination of one or more exceeded or non-exceeded thresholds may be determinative of lock out of the operator from the instrument.

An advantage of the data tracking system 310 is that it may automatically track operator compliance for a plurality of operators. Furthermore, each portable test instrument 102 may be configured to communicate each sample test result and operator identity to the results store 315 in the data tracking system 310. This may allow for the data tracking system 310 to generate an events profile 330 for each operator, including compliant events and non-compliant events. For example, an events profile may include, in addition to the operator's identity, a set of event records for evaluations performed for that operator with respect to each attribute, e.g., each of the College of American Pathologists' competency requirements, including where applicable the date and time performed, the name of the evaluator, the elements or skills evaluated, and the assessment of competency level or compliance. Note also that the results store 315 may further comprise a store for knowledge tests, quality control tests, and/or proficiency tests performed by the operator using the instrument or remote device. Therefore, some embodiments of the present invention may be implemented for portable test instruments that perform tests on a blood sample contained in a single-use cartridge, which mates with the instrument, generally where the cartridge contains electrochemical sensors or optical assays (as described above with reference to FIG. 1).

Instrument and Cartridge Operator Competency and Compliance Monitoring Method

Figure 5:
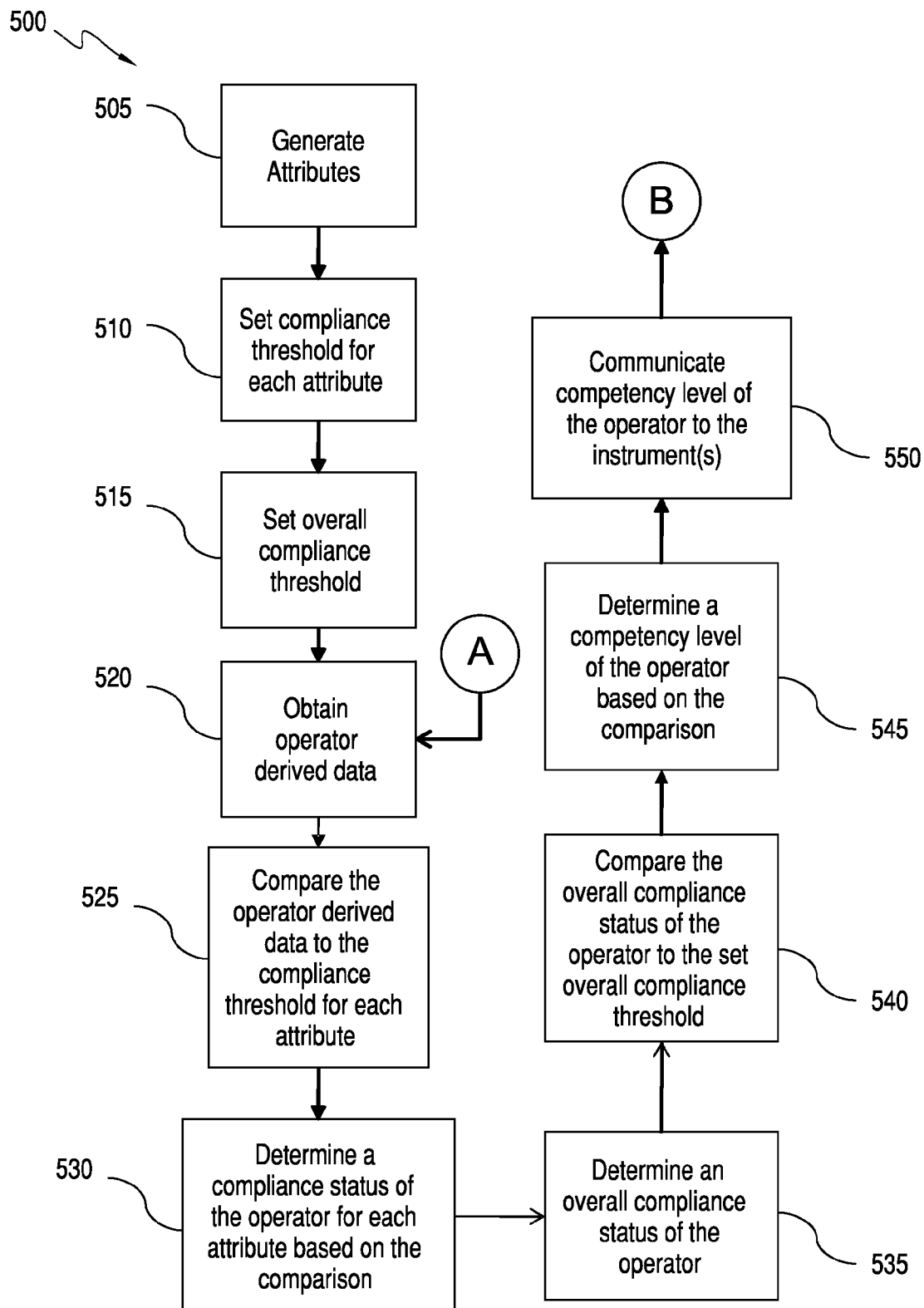
FIGS. 5 and 6 are illustrative process flow diagrams for implementing the system in accordance with some aspects of the invention.
Figure 6:
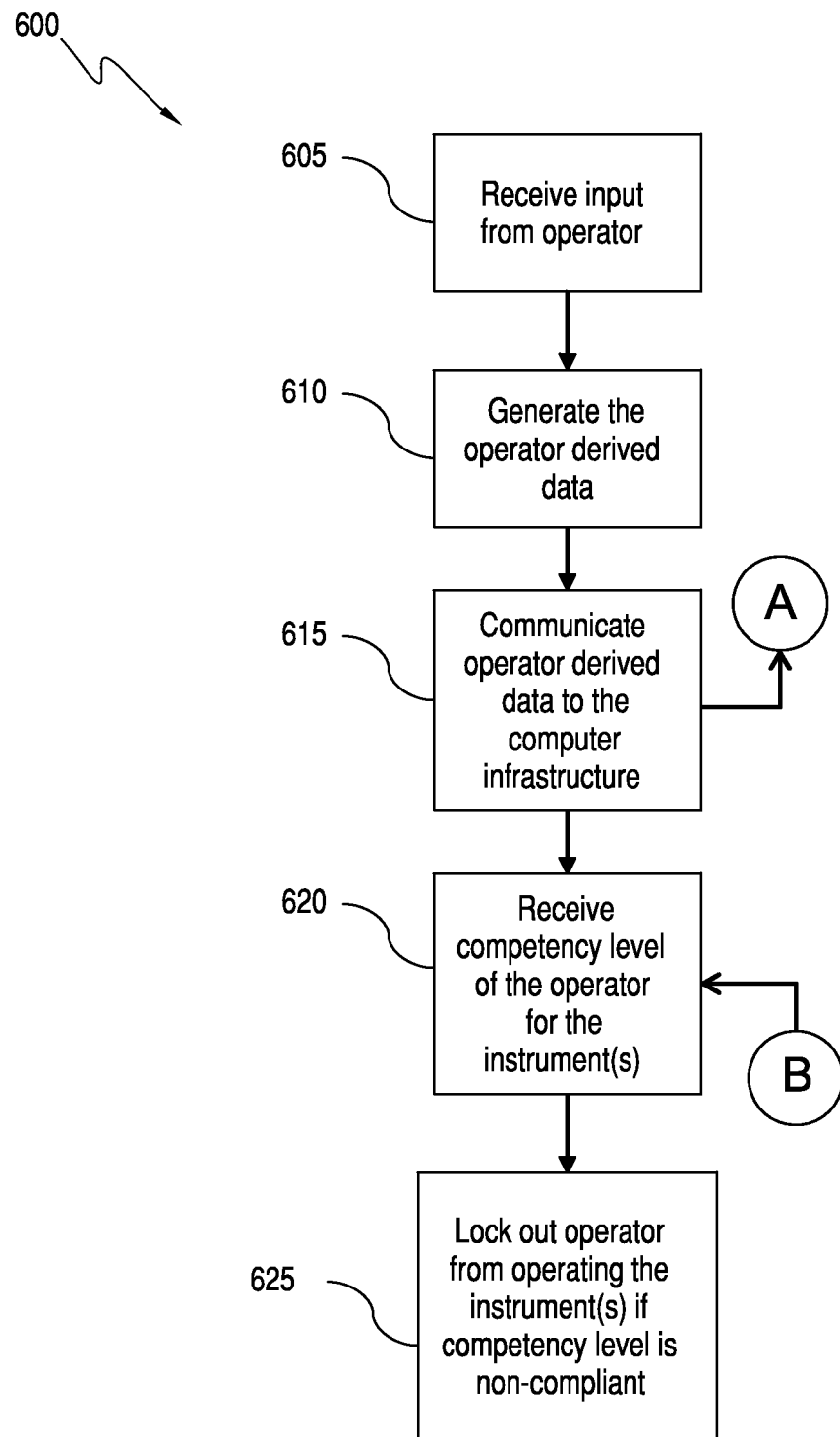

FIGS. 5 and 6 show exemplary flowcharts for performing the process steps of the present invention. The steps of FIGS. 5 and 6 may be implemented using the computing device described above with respect to FIGS. 1-4. Specifically, the flowcharts in FIGS. 5 and 6 illustrate the architecture, functionality, and operation of possible implementations of the systems, methods and computer program products according to several embodiments of the present invention. In this regard, each block in the flowcharts may represent a module, segment, or portion of code, which comprises one or more executable instructions for implementing the specified logical function(s). It should also be noted that, in some alternative implementations, the functions noted in the blocks may occur out of the order noted in the figure. For example, two blocks shown in succession may, in fact, be executed substantially concurrently, or the blocks may sometimes be executed in the reverse order, depending upon the functionality involved. It will also be noted that each block of the flowchart illustrations, and combinations of blocks in the flowchart illustrations, can be implemented by special purpose hardware-based systems that perform the specified functions or acts, or combinations of special purpose hardware and computer instructions.

In one embodiment of the present invention, the computing device may be configured to assess the competency of an operator to operate at least one sample testing instrument. As shown in FIG. 5, a process 500 may be provided for compliance monitoring. At step 505, a plurality of attributes may be generated to assess a competency level of the operator to operate the at least one sample testing instrument. For example, the quality compliance manager may select predetermined attributes provided by a service provider to implement initial training and/or ongoing assessment of an operator's testing competency on the at least one sample testing instrument. The operator may be a non-laboratorian (e.g., a nurse or doctor) and the at least one sample testing instrument may be a reading apparatus (as discussed with reference to FIG. 1).

In alternative or additional embodiments, the quality compliance manager may generate or set their own attributes and/or customize, update, or set default templates of attributes. The new or customized attributes may therefore be generated specific to each operator or group of operators (e.g., Intensive Care Unit nurses).

In some embodiments, generating the plurality of attributes may comprise selecting a number of attributes (e.g., selecting at least two attributes). The number of attributes may comprise a knowledge test for operation of the at least one instrument, a knowledge test for biological sample acquisition and disposition with the at least one instrument, a knowledge test on biological sample testing regulations, a practical test on obtaining biological sample test results with the at least one instrument, a practical test on quality control testing with the at least one instrument, and/or a practical test on data entry and data handling with the at least one instrument.

In additional embodiments, the number of attributes may comprise direct observation of routine patient test performance, including testing performance and monitoring the recording of the results (e.g., this may include recording all test results performed by the operator on a sample testing instrument and monitoring the results for any instrument reported errors). The plurality of attributes may also include the review of intermediate test results, quality control results, proficiency testing results, and preventive maintenance records (e.g., this may include recording all of these results performed by the operator and monitoring the results for inaccuracies or errors). The plurality of attributes may also include observation of performance of instrument maintenance and function checks (e.g., this may include recording the results of knowledge tests for operation of the at least one instrument and/or training sessions on the at least one instrument). The plurality of attributes may also include the assessment of problem solving skills (e.g., this may include recording the results of knowledge tests for biological sample acquisition and disposition with the at least one instrument and knowledge tests on biological sample testing regulations).

In accordance with some aspects of the present invention, the attributes may comprise an electronic signature element. The electronic signature may be configured to provide an indication as to whether the user adopts the contents of the attributes, or the user who claims to have generated the attributes is the one who generated the attributes. For example, the electronic signature may be configured to provide an indication that the quality compliance manager generated or approved the attributes.

In accordance with additional aspects of the present invention, the attributes may comprise an electronic log event element. The electronic log event element may be configured to store related information. For example, the electronic log event element may be configured to store the compliance status and competency level for the operator.

At step 510, a compliance threshold for each attribute of the plurality of attributes may be set (e.g., a quality compliance manager may input thresholds for each attribute based on Point of Care Testing Policies established at a medical facility). In some embodiments, the compliance threshold may be set as a predetermined score (e.g., 80 out of 100) required for passing a knowledge test. In alternative embodiments, the compliance threshold may be set as a predetermined number of errors (e.g., 5 errors pertaining to an incorrect sample being used for a specified device or cartridge) within a predetermined amount of time or predetermined number of analytical tests run. In additional or alternative embodiments, the compliance thresholds may be provided by a service provider or compliance regulatory organization (e.g., College of American Pathologists).

At step 515, an overall compliance threshold may be set for the at least one sample testing instrument. For example, the quality compliance manager may determine a level of sophistication or knowledge required to operate the at least one sample testing instrument and set the overall compliance threshold accordingly.

At step 520, operator derived data pertaining to the operators ability to operate the at least one sample testing instrument may be obtained. In some embodiments, the operator derived data may include a number (e.g., two) of attribute test results obtained by the operator. The attribute test results may include analytical test results, control test results, proficiency test results, and/or knowledge or training test results. In some embodiments, the analytical test results, the control test results, and the proficiency test results may be communicated or provided to the data manager via the at least one sample testing instrument. In other words, the sample testing instrument may communicate or provide the analytical test results, the control test results, and the proficiency test results upon the operator operating the sample testing instrument to perform testing analysis.

In additional or alternative embodiments, the knowledge or training test results may be communicated or provided by the quality compliance manager or a remote computing device such as a personal computer comprising an application configured to present the knowledge or training test to the operator. As should be understood by one of ordinary skill in the art, the aforementioned results may be provided to the data manager using any sample testing instrument or computing device in accordance with some aspects of the present invention.

In some embodiments, the test results (e.g., analytical test results, control test results, proficiency test results, and/or knowledge or training test results) may be linked to a corresponding operator identifier configured to identify the operator that performed or took the test. For example, the operator identifier may be embedded within metadata of the test results or saved together in a table format. In these embodiments, obtaining the operator derived data may also comprise receiving the operator identifier.

Optionally, an event profile for the operator may be generated that comprises the test results and is linked to the operator identifier such that the event profile is specific to the operator. In some embodiments, the event profile may also comprise the determined compliance status of the operator for each attribute and the competency level of the operator for the at least one sample testing instrument.

In some embodiments, new operator derived data may be obtained and used to continuously update the event profile including the compliance status for each attribute and the competency level of the operator for the at least one sample testing instrument. The competency status and the competency level may comprise a preset limited duration or expiration such that the competency status and competency level of the operator should be reevaluated after expiration.

In accordance with some aspects of the present invention, the operator identifier may be a password, a alpha-numerical or numerical code, a biometric identifier, an RFID tag or a barcode.

At step 525, the operator derived data may be compared to the set compliance threshold for each attribute of the plurality of attributes. For example, one of the attributes may be set as a knowledge test for biological sample acquisition. The operator derived data obtained may comprise results from the operator taking the knowledge test. Those results may be compared to the set compliance threshold for the knowledge test (e.g., the operator may have obtained an 85% on the knowledge test and the compliance threshold may have been set at 80%; thus, the data manager or tracking system compares the two variables).

At step 530, a compliance status of the operator for each attribute based on the comparison of the operator derived data to the set compliance thresholds may be determined. For example, if the knowledge test result of an 85% is greater than the compliance threshold of 80%, then the data manager may determine that the operator is compliant for that attribute. In some embodiments, if the analytical test results comprise a number of errors greater than the set compliance threshold, then the data manager may determine that the operator is non-compliant for that an attribute pertaining to patient test performance.

In accordance with some aspects of the present invention, determining the compliance status of the operator may comprise determining whether the electronic signature element for each attribute is completed by an authorized user (e.g., quality compliance manager). Additionally, determining the compliance status of the operator may comprise recording the compliance status and/or competency level of the operator in the electronic log event element.

At step 535, an overall compliance status of the operator may be generated based on the determined compliance status of the operator for each attribute. For example, the data manager may review the determined compliance statuses for each attribute to determine an overall grade for the operator. In some embodiments, the overall compliance status may be generated based on a sum of all of the compliant or non-compliant statuses determined for each attribute.

At step 540, the overall compliance status of the operator may be compared to the set overall compliance for the at least one sample testing instrument. For example, the sum of all compliant or non-compliant statuses may be compared to a threshold level of overall compliance or non-compliance for the at least one sample testing instrument.

At step 545, a competency level of the operator for the at least one sample testing instrument may be determined based on the comparison of the overall compliance status of the operator to the set overall compliance threshold. For example, the competency level of the operator may be determined to be compliant if the sum of all compliant statuses is greater than the threshold level of overall compliance for the at least one sample testing instrument.

In some embodiments, the set overall compliance threshold may comprise any combination of at least a number (e.g., two) of attributes having a non-approved compliance status. Determining the competency level may comprise determining the competency level of the operator to be non-compliant when the overall compliance status includes at least a number of attributes having a non-approved compliance status, and determining the competency level of the operator to be compliant when the overall compliance status includes less than a number of attributes having a non-approved compliance status.

In alternative embodiments, the set overall compliance threshold may comprise any combination of at least a number (e.g., two) of attributes having an approved compliance status. Determining the competency level may comprise determining the competency level of the operator to be compliant when the overall compliance status includes at least a number of attributes having an approved compliance status, and determining the competency level of the operator to be non-compliant when the overall compliance status includes less than a number of attributes having an approved compliance status.

In alternative embodiments, the set overall compliance threshold may comprise a statistical combination of the plurality of attributes having an approved compliance status and a non-approved compliance status. Determining the competency level may comprise determining the competency level of the operator to be compliant when the overall compliance status is equal to or exceeds the statistical combination of the plurality of attributes, and determining the competency level of the operator to be non-compliant when the overall compliance status is less than the statistical combination of the plurality of attributes.

In alternative embodiments, the set overall compliance threshold may comprise a statistical combination of the plurality of attributes having an approved compliance status and a non-approved compliance status. Determining the competency level may comprise determining the competency level of the operator to be non-compliant when the overall compliance status is equal to or exceeds the statistical combination of the plurality of attributes, and determining the competency level of the operator to be compliant when the overall compliance status is less than the statistical combination of the plurality of attributes.

At step 550, the determined competency level of the operator may be communicated to the at least one sample testing instrument. For example, the data manager may send a competency level to at least one sample testing instrument via the computer infrastructure.

As should be understood by one of ordinary skill in the art, one or more steps in the process described in connection with FIG. 5 may occur simultaneously or substantially simultaneously with other process steps and/or the order of the steps may be modified.

In one embodiment of the present invention, the biological sample test system may be configured to perform at least one analytical test on an instrument and automatically lock out an operator from operating the instrument based on the competency level of the operator. As shown in FIG. 6, a process 600 may be provided for generating operator derived data on an instrument and locking out a user from operating the instrument. Optionally at step 605, the instrument may be configured to receive input from an operator (e.g., an operator identifier), which may comprise the operator derived data. At step 610, the instrument may be configured to generate the operator derived data. For example, the operator may operate the instrument to analyze a biological sample on the instrument, perform a proficiency test on the instrument, perform a knowledge test on the instrument, perform a control test on the instrument, etc. In some embodiments, the instrument may be configured to determine the result of the test(s) performed by the operator on the instrument (e.g., an analytical test result), which may comprise the operator derived data. In additional embodiments, any errors determined by the instrument during the operation may also be determined as operator derived data.

At step 615, the instrument may be configured to communicate the operator derived data to the system infrastructure (e.g., the data manger 104 as discussed with respect to FIG. 1). At step 620, the instrument may be configured to receive the determined competency level of the operator for the instrument(s). At step 625, the instrument may be configured to lock out the operator from operating the instrument(s) if the competency level is non-compliant.

As should be understood by one of ordinary skill in the art, one or more steps in the process described in connection with FIG. 6 may occur simultaneously or substantially simultaneously with other process steps and/or the order of the steps may be modified.

In some embodiments, a service provider, such as the biological sample test system provider, could offer to perform all or some of the processes described herein. In this case, the service provider can create, maintain, deploy, support, etc., the computer infrastructure that performs the all or some of the process steps of the invention for one or more customers. These customers may be, for example, any business that uses the point of care technology. In return, the service provider can receive payment from the customer(s) under a subscription and/or fee agreement.

While the invention has been described in terms of various preferred embodiments, those skilled in the art will recognize that various modifications, substitutions, omissions and changes can be made without departing from the spirit of the present invention. It is intended that the scope of the present invention be limited solely by the scope of the following claims. In addition, it should be appreciated by those skilled in the art that a plurality of the various embodiments of the invention, as described above, may be coupled with one another and incorporated into a single reader device.

We claim:

1. A method implemented in a computer infrastructure having computer executable code tangibly embodied on a computer readable storage medium having programming instructions operable to:

generate a plurality of attributes configured to assess a competency level of an operator to operate at least one sample testing instrument operable to perform an analytical test;
set a compliance threshold for the at least one sample testing instrument;
obtain operator derived data pertaining to the operator's ability to operate the at least one sample testing instrument, wherein the operator derived data comprises at least two attribute test results obtained by the operator;
determine a compliance status of the operator for each of at least two attributes of the plurality of attributes based on a comparison of each of the obtained at least two attribute test results to a set compliance status threshold for each of at least two attributes, respectively;
determine an overall compliance status of the operator based on the determined compliance status of the operator for each of the at least two attributes;
determine the competency level of the operator for the at least one sample testing instrument based on a comparison of the overall compliance status of the operator to the set compliance threshold; and
communicate the competency level of the operator to the at least one sample testing instrument, wherein when the competency level of the operator is indicative of non-compliance, the competency level causes the at least one sample testing instrument to lock out the operator from operating the at least one sample testing instrument,
wherein the generating the plurality of attributes comprises receiving a selection of the at least two attributes from the group consisting of: a knowledge test for operation of the at least one instrument, a knowledge test for biological sample acquisition and disposition with the at least one instrument, a knowledge test on biological sample testing regulations, a practical test on obtaining biological sample test results with the at least one instrument, a practical test on quality control testing with the at least one instrument, a practical test on data entry and data handling with the at least one instrument,
wherein the at least one instrument comprises a disposable device, operating in conjunction with a hand-held analyzer, for performing the analytical test on blood or other fluids, and
wherein the analytical test is at least one selected from the group consisting of: oxygen, carbon dioxide, pH, potassium, sodium, chloride, hematocrit, glucose, urea, creatinine, prothrombin time (PT), activated clotting time (ACT), activated partial thromboplastin time (APTT), cardiac troponin I (cTnI), brain natriuretic peptide (BNP), creatine kinase MB (CKMB) and lactate.

2. The method of claim 1, wherein:
the at least two attribute test results are linked to a corresponding operator identifier configured to identify the operator; and
the obtaining the operator derived data comprises receiving the at least two attribute test results and the operator identifier.

3. The method of claim 2, wherein:
the at least two attribute test results comprise a knowledge test result obtained by the operator participating in a knowledge test or training session;
the knowledge test result is linked to the corresponding operator identifier configured to identify the operator; and
the obtaining the operator derived data further comprises receiving the knowledge test result and the operator identifier from at least one of the at least one sample testing instrument and a computing device.

4. The method of claim 3, wherein:
the programming instructions are further operable to generate an event profile for the operator;
the event profile comprises the at least two attribute test results and the event profile is linked to the operator identifier configured to identify the operator;
the event profile further comprises the compliance status of the operator for each of the at least two attributes and the competency level of the operator for the at least one instrument;
the compliance status of the operator for each of the at least two attributes comprises a preset limited duration; and
the programming instructions are further operable to receive new operator derived data and continuously update the event profile including the compliance status of the operator for each of the at least two attributes and the competency level of the operator based on the received new operator derived data.

5. The method of claim 1, wherein:
each attribute of the plurality of attributes comprises an electronic signature element; and
the determining the compliance status of the operator for each of at least two attributes further comprises determining whether the electronic signature element for each attribute is completed by an authorized user.

6. The method of claim 5, wherein:
each attribute of the plurality of attributes comprises an electronic log event element; and
the determining the compliance status of the operator for each of the at least two attributes further comprises recording the compliance status of the operator for each of the at least two attributes in the electronic log event element.

7. The method of claim 1, wherein the generating the plurality of attributes comprises setting each of the plurality of attributes to a default template.

8. The method of claim 1, wherein:
the set compliance threshold comprises any combination of the at least two attributes having a non-approved compliance status; and
the determining the competency level comprises:
when the overall compliance status includes the at least two attributes having a non-approved compliance status, determining the competency level to be non-compliant; and
when the overall compliance status includes less than the at least two attributes having a non-approved compliance status, determining the competency level to be compliant.

9. The method of claim 1, wherein:
the set compliance threshold comprises any combination of the at least two attributes having an approved compliance status; and
the determining the competency level comprises:
when the overall compliance status includes the at least two attributes having an approved compliance status, determining the competency level to be compliant; and
when the overall compliance status includes less than the at least two attributes having a non-approved compliance status, determining the competency level to be non-compliant.

10. The method of claim 1, wherein:
the set compliance threshold comprises a statistical combination of the plurality of attributes having an approved compliance status and a non-approved compliance status; and
the determining the competency level comprises:
when the compliance status is equal to or exceeds the statistical combination of the plurality of attributes, determining the competency level to be compliant; and
when the compliance status is less than the statistical combination of the plurality of attributes, determining the competency level to be non-compliant.

11. The method of claim 1, wherein:
the set compliance threshold comprises a statistical combination of the plurality of attributes having an approved compliance status and a non-approved compliance status; and
the determining the competency level comprises:
when the compliance status is equal to or exceeds the statistical combination of the plurality of attributes, determining the competency level to be non-compliant; and
when the compliance status is less than the statistical combination of the plurality of attributes, determining the competency level to be compliant.

12. The method of claim 1, wherein a service provider at least one of creates, maintains, deploys and supports the computer infrastructure.

13. The method of claim 1, wherein steps of claim 1 are provided by a service provider on a subscription and/or fee basis.

14. A system implemented in hardware, comprising:
a tracking module configured to:
generate a plurality of attributes configured to assess a competency level of an operator to operate at least one sample testing instrument operable to perform an analytical test;
set a compliance threshold for the at least one sample testing instrument;
obtain operator derived data pertaining to the operator's ability to operate the at least one sample testing instrument, wherein the operator derived data comprises at least two attribute test results obtained by the operator;
determine a compliance status of the operator for each of at least two attributes of the plurality of attributes based on a comparison of each of the obtained at least two attribute test results to a set compliance status threshold for each of at least two attributes, respectively;
determine an overall compliance status of the operator based on the determined compliance status of the operator for each of the at least two attributes;
determine the competency level of the operator for the at least one sample testing instrument based on a comparison of the overall compliance status of the operator to the set compliance threshold; and
communicate the competency level of the operator to the at least one sample testing instrument, wherein when the competency level of the operator is indicative of non-compliance, the competency level causes the at least one sample testing instrument to lock out the operator from operating the at least one sample testing instrument,
wherein the generating the plurality of attributes comprises receiving a selection of the at least two attributes from the group consisting of: a knowledge test for operation of the at least one instrument, a knowledge test for biological sample acquisition and disposition with the at least one instrument, a knowledge test on biological sample testing regulations, a practical test on obtaining biological sample test results with the at least one instrument, a practical test on quality control testing with the at least one instrument, a practical test on data entry and data handling with the at least one instrument,
wherein the at least one instrument comprises a disposable device, operating in conjunction with a hand-held analyzer, for performing the analytical test on blood or other fluids, and
wherein the analytical test is at least one selected from the group consisting of: oxygen, carbon dioxide, pH, potassium, sodium, chloride, hematocrit, glucose, urea, creatinine, calcium, prothrombin time (PT), activated clotting time (ACT), activated partial thromboplastin time (APTT), cardiac troponin I (cTnI), brain natriuretic peptide (BNP), creatine kinase MB (CKMB) and lactate.

15. The system of claim 14, wherein:
the at least two attribute test results are linked to a corresponding operator identifier configured to identify the operator; and
the obtaining the operator derived data comprises receiving the at least two test attribute results and the operator identifier.

16. The system of claim 15, wherein:
the at least two attribute test results comprise a knowledge test result obtained by the operator participating in a knowledge test or training session;
the knowledge test result is linked to the corresponding operator identifier configured to identify the operator; and
the obtaining the operator derived data further comprises receiving the knowledge test result and the operator identifier from at least one of the at least one sample testing instrument and a computing device.

17. The system of claim 16, wherein:
the tracking module is further configured to generate an event profile for the operator; and
the event profile comprises the at least two attribute test results and the event profile is linked to the operator identifier configured to identify the operator.

18. A computer program product comprising a non-transitory computer readable storage medium having readable program code embodied in the storage medium, the computer program product includes at least one component operable to:
generate a plurality of attributes configured to assess a competency level of an operator to operate at least one sample testing instrument operable to perform an analytical test;
set a compliance threshold for the at least one sample testing instrument;
obtain operator derived data pertaining to the operator's ability to operate the at least one sample testing instrument, wherein the operator derived data comprises at least two attribute test results obtained by the operator;
determine a compliance status of the operator for each of at least two attributes of the plurality of attributes based on a comparison of each of the obtained at least two attribute test results to a set compliance status threshold for each of at least two attributes, respectively;

determine an overall compliance status of the operator based on the determined compliance status of the operator for each of the at least two attributes;

determine the competency level of the operator for the at least one sample testing instrument based on a comparison of the overall compliance status of the operator to the set compliance threshold; and communicate the competency level of the operator to the at least one sample testing instrument, wherein when the competency level of the operator is indicative of non-compliance, the competency level causes the at least one sample testing instrument to lock out the operator from operating the at least one sample testing instrument, wherein the generating the plurality of attributes comprises receiving a selection of the at least two attributes from the group consisting of: a knowledge test for operation of the at least one instrument, a knowledge test for biological sample acquisition and disposition with the at least one instrument, a knowledge test on biological sample testing regulations, a practical test on obtaining biological sample test results with the at least one instrument, a practical test on quality control testing with the at least one instrument, a practical test on data entry and data handling with the at least one instrument, wherein the at least one instrument comprises a disposable device, operating in conjunction with a hand-held analyzer, for performing the analytical test on blood or other fluids, and wherein the analytical test is at least one selected from the group consisting of: oxygen, carbon dioxide, pH, potassium, sodium, chloride, hematocrit, glucose, urea, creatinine, calcium, prothrombin time (PT), activated clotting time (ACT), activated partial thromboplastin time (APTT), cardiac troponin I (cTnI), brain natriuretic peptide (BNP), creatine kinase MB (CKMB) and lactate.

* * * * *